United States Patent [19]

Young

[11] Patent Number: 4,575,260

[45] Date of Patent: Mar. 11, 1986

[54] THERMAL CONDUCTIVITY PROBE FOR FLUID IDENTIFICATION

[75] Inventor: Allen R. Young, Duncan, Okla.

[73] Assignee: Halliburton Company, Duncan, Okla.

[21] Appl. No.: 608,838

[22] Filed: May 10, 1984

[51] Int. Cl.$^4$ .................. E21B 47/06; G01K 13/00
[52] U.S. Cl. ................................ 374/136; 73/154; 374/44
[58] Field of Search ............ 374/43, 44, 29, 31, 374/10, 136; 73/154

[56] References Cited

U.S. PATENT DOCUMENTS

| | | | |
|---|---|---|---|
| 2,382,609 | 8/1945 | Dale | 374/186 X |
| 2,787,906 | 4/1957 | Piety | 374/136 X |
| 3,044,298 | 7/1962 | Hodges et al. | 73/154 X |
| 3,164,988 | 1/1965 | Cook | 73/154 |
| 3,597,636 | 8/1971 | Moore | 374/31 |
| 3,668,927 | 6/1972 | Howell et al. | 73/154 |
| 3,698,812 | 10/1972 | Nelson | 356/5 |
| 3,807,227 | 4/1974 | Smith, Jr. | 73/154 |
| 3,864,969 | 2/1975 | Smith, Jr. | 73/154 |
| 3,981,187 | 9/1976 | Howell | 374/29 X |
| 4,264,907 | 4/1981 | Durand et al. | 343/6 ND |

FOREIGN PATENT DOCUMENTS 2286365 4/1976 France .

Primary Examiner—Daniel M. Yasich
Attorney, Agent, or Firm—William J. Beard

[57] ABSTRACT

For use with a sonde adapted to be lowered into a well borehole, the sonde supports a thermal conductivity probe response to well fluid thermal conductivity. In the preferred and illustrated embodiment, a four leg resistor bridge circuit has two temperature-sensitive legs exposed to well fluid. In addition, one such bridge leg is positioned adjacent to a heater dissipating constant heat power. The remaining leg is exposed to ambient well fluid. The bridge incremental voltage varies with the ambient temperature of the well fluid, but such ambient variations are compensated for by the remaining temperature-sensitive leg which causes nulling of ambient temperature changes. The heat transferred to the heated bridge leg determines the incremental voltage and, hence, the conductivity of fluid in the well bore can be measured.

6 Claims, 5 Drawing Figures

THERMAL CONDUCTIVITY PROBE FOR FLUID IDENTIFICATION

BACKGROUND OF THE DISCLOSURE

This apparatus relates to a detector system for determining thermal conductivity of fluids in a well bore. A sonde suspended on a logging cable is lowered to the bottom of a well. The sonde encounters various fluids in the well bore. Identification of the fluids is enhanced by determining the thermal conductivity of the fluids and, hence, fluid identification can thereby be obtained. Typically, thermal conductivity is measured in BTU/Hour/Foot Square/Degree F/Foot and for water is 0.3263 at 72° F. For transformer oil, it is 0.103 and for kerosene, it is 0.086..The thermal conductivity for methane gas is 0.0175 and for air, it is 0.014. It can be understood on noting these values of thermal conductivity that the fluid media surrounding the sonde determines the rate of heat transfer away from the sonde.

It is, however, difficult to measure thermal conductivity of the fluids adjacent to the sonde because the ambient temperature increases more or less as a function of depth ignoring geothermal wells. Accordingly, wells as deep as 15,000 to 20,000 feet are quite hot. Because of the change in ambient temperature, measurements based on relative temperature are difficult to obtain, and such temperature measurements cannot be easily isolated or separated in thermal conductivity measurements. The apparatus that this disclosure sets forth a thermal conductivity probe adapted to be incorporated in the sonde. When the sonde is lowered into the well, it is exposed to ever increasing ambient temperatures. This apparatus utilizes a resistor bridge having four legs. Two of the legs are fixed. Two of the legs include resistor elements which are both physically mounted so that they are exposed to the well fluid. Thus, the two legs exposed to well fluid will commonly drift as a function of temperature. That is, the resistance in each leg will be different as a function of the ambient temperature. Since the same ambient temperature drift is observed in both legs, the drift in the output voltage of the resistor bridge is nil and does not drift as a function of ambient temperature. This then enables the resistor bridge to obtain measurements relating to thermal conductivity.

Thermal conductivity can thus be determined by observation of down hole bridge differential voltages. Moreover, transitions between fluid media in the well bore can be observed. For instance, assume that the device of this disclosure is lowered into a well bore which has a standing column of liquid. Assume that the column is oil from the formation which has separated and which stands on top of a column of water. A sonde supporting a thermal conductivity probe in accordance with the teachings of this disclosure, if lowered in the well bore, will detect the oil and water interface in the column of liquid standing in the well. Thus, the measurement of thermal conductivity will deflect significantly on crossing the interface between oil and water. It will also deflect significantly on crossing the interface between the oil and air or methane above the oil. Such changes can be observed and hence the location of oil and water in the well bore can be determined. Moreover, thermal conductivity of mixtures can also be determined.

With the foregoing in view, the present apparatus is described a thermal conductivity probe adapated to be lowered into a well bore hole for measurement of thermal conductivity of fluids in the well, including both gases and liquids. The device is adapted to be exposed to temperature gradients in the well and yet provides an output reading which is not altered by the ambient temperature variation. Many advantages flow from use of the thermal conductivity probe incorporated in a sonde as set forth in this disclosure.

BRIEF DESCRIPTION OF THE DRAWINGS

So that the manner in which the above recited features, advantages and objects of the present invention are attained and can be understood in detail, more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

FIG. 3 is a heat sink mounting for a resistor comprising a part of the resistor bridge shown in FIG. 2 which is exposed to well fluids in the bore hole;

FIG. 4 is a sectional view along the Line 4—4 of FIG. 3 showing details of mounting of the heat sink and bridge resistor.

DETAILED DESCRIPTION OF THE PREFERRED EMBODIMENT

Figure 1:
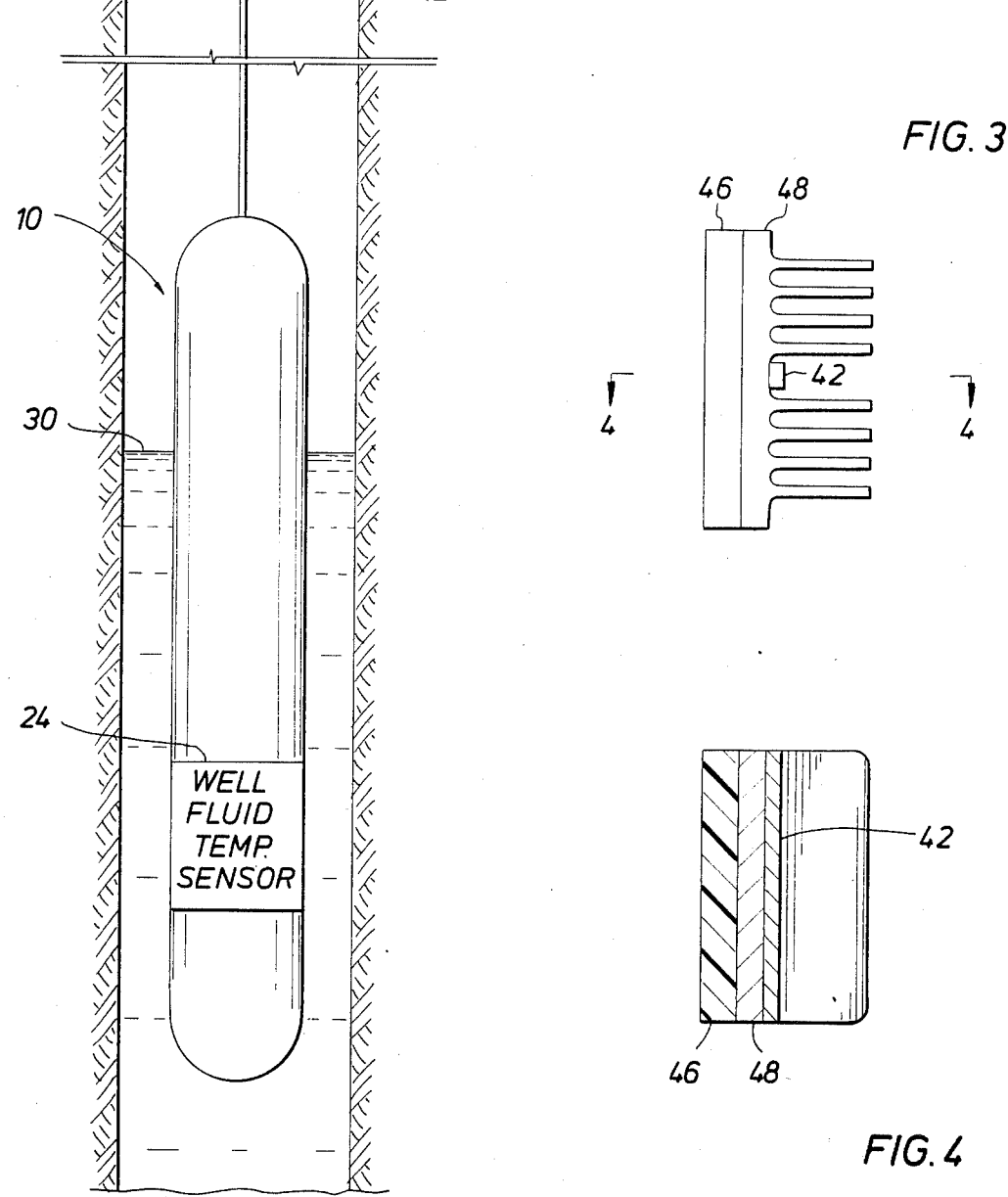
FIG. 1 of the drawings shows a sonde in a well bore which incorporates a well fluid temperature sensor in accordance with the teachings of this disclosure.

Attention is first directed to FIG. 1 of the drawings where a sonde 10 is lowered in a well bore hole 12 for measuring thermal conductivity of the fluids in the bore hole. A sonde 10 is supported on a logging cable 14 and is lowered to the bottom of the bore hole 12. The well might be quite deep; typically, the sonde is lowered to the bottom of the well and is retrieved by retracting the logging cable 14. It passes over sheave 16, and the logging cable 14 is stored on a drum 18. The drum 18 spools the cable to store it. One or more suitable conductors in the logging cable 14 provides output data signals to equipment at the surface, and a conductor 20 is input a data processor 22. The cable 20 enables signals to be furnished from a well fluid temperature sensor 24 carried in the sonde 10. The data processor 22 puts the signal indicative of thermal conductivity in suitable form and supplies the signal to a recorder 26. The recorder records the signal as a function of sonde depth in the well 12. Depth is determined by means of an electrical or mechanical depth measuring instrument 28 which is connected to the sheave 16 to determine depth of the sonde in the well 12. FIG. 1 shows the sonde lowered in the well to the extent that it encounters a standing column of liquid in the well, the liquid interface being identified at 30. Assume for purposes of discussion that the liquid 30 is water and that the remainder of the well 12 is filled with air.

Figure 2:
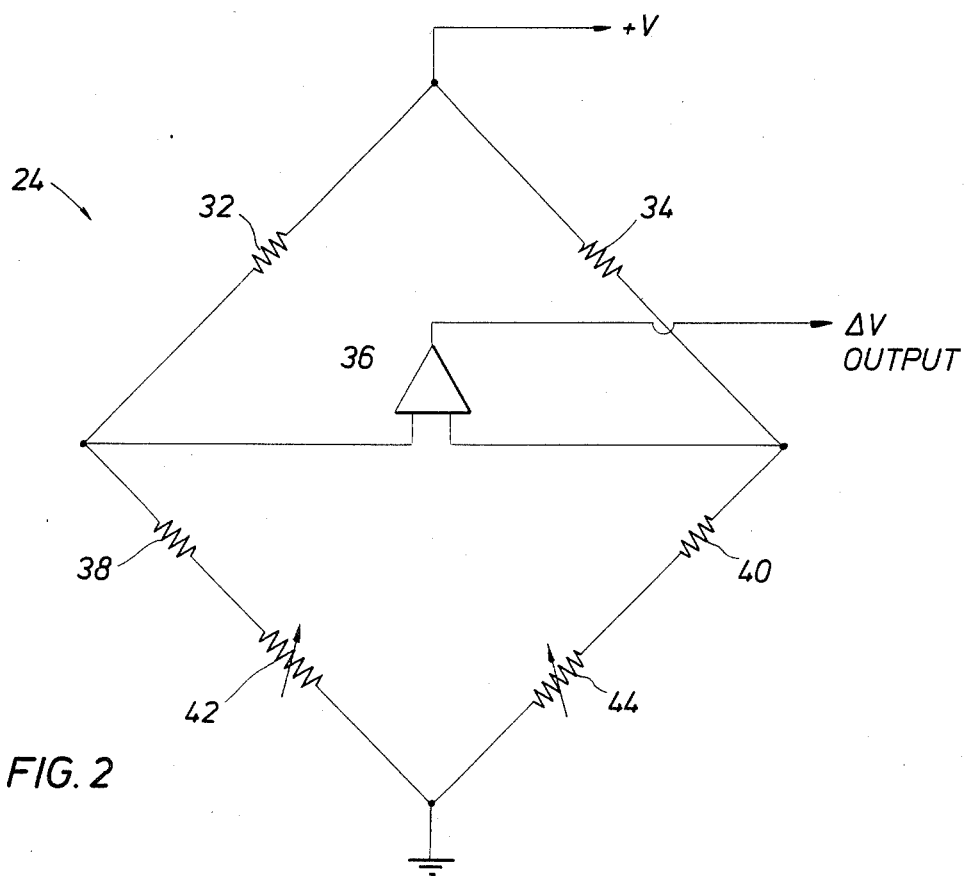
FIG. 2 shows a resistor bridge having four legs forming an output voltage which is indicative of the thermal conductivity of fluids in the well bore.

Attention is directed to FIG. 2 of the drawings where the well fluid temperature sensor 24 is shown in schematic form. There, the schematic sets out a bridge circuit. The bridge has four legs, and preferably all four legs are formed of resistive elements. Thus, the bridge circuit incorporates a first fixed leg 32 and a similar fixed resistor leg 34. The bridge circuit is connected to a suitable voltage source, typically between 5 and 15 volts dc. The bridge has two mid-points which are connected as inputs to a differential amplifier 36. It forms an output signal which is denoted as the incremental output voltage. This voltage is indicative of the thermal conductivity as will be described.

The bridge circuit shown in FIG. 2 is grounded at the corner opposite the B+ voltage. The bridge circuit includes additional bridge legs which include fixed resistors 38 and 40. These resistors are included to protect against shorting and control the range of deflection and signal end points for operation of the bridge circuit output signal. The numeral 42 identifies a first temperature sensitive resistor. It is represented by a symbol indicative of the fact that it is a variable resistor. It is not a variable resistor in the form of a potentiometer; rather, it is a resistor made variable by its exposure to the fluids in the well. The resistor 42 is similar to a second variable resistor 44, and the resistors 42 and 44 are both exposed to well fluids as will be described.

The resistors 42 and 44 are located on the exterior of the sonde where they are exposed to the fluids in the well. Alternatively, they can be recessed internally of the sonde and exposed to well fluids by positioning the resistors 42 and 44 where they are substantially surrounded by well fluid. For instance, ports constructed in the sonde may divert fluid in the well bore to the vicinity of the resistors 42 and 44. Preferably, they are physically mounted so that they are exposed to the same fluid in the well bore and, hence, are preferably maintained at the same relative elevation on the sonde 10.

FIG. 3 shows a mounting for the exposed resistors. The mounting of FIG. 3 is particularly intended for the resistor 42. The mounting for the resistor 44 is similar and will be discussed with a description of FIG. 5. In FIG. 3 of the drawings, the numeral 46 identifies a mounting pad. This pad is preferably made of an insulated material, and mounts the resistor on the sonde. The mounting pad 46 has a specified size and is adapted to receive a heat sink 48 which is mounted thereon. The heat sink is preferably formed of aluminium in the typical case and is equipped with a number of fins which protrude from the heat sink to dissipate heat. The fin-equipped heat sink has a specified surface area to enable heat dissipation to occur. Moreover, the heat sink is equipped with a number of fins around a mounting location thereon for receipt of the resistor 42. The resistor 42 is preferably encapsulated in a suitable material, typically epoxy resin. The resistor 42 is thus mounted in intimate contact with the heat sink 48. The heat sink 48 aids and assists in assuring that the resistor 42 assumes the same temperature as the fluid media adjacent to the heat sink 48. The size and distribution of the fins in the total surface area of the heat sink 48 can be selected to assure that the heat sink serves the intended purpose. The heat sink 48 is shown in sectional view in FIG. 4 wherein the resistor 42 is again shown mounted between adjacent fins.

Figure 5:
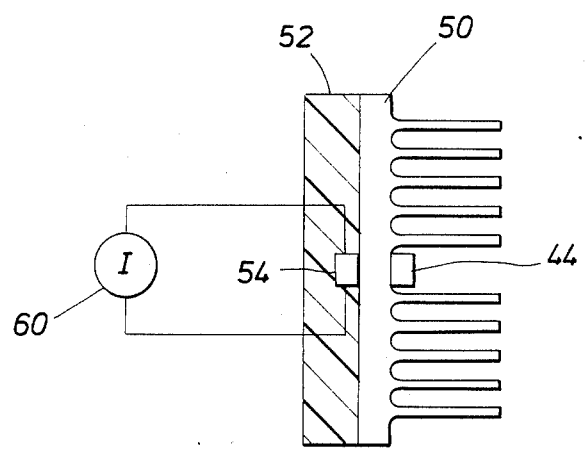
FIG. 5 is a view similar to FIG. 3 showing details of mounting of a second resistor in the bridge circuit of FIG. 2 including a heater for the resistor element.

Attention is next directed to FIG. 5 of the drawings which shows a modified heat sink construction. In FIG. 5, the mounting pad 52 is shown for supporting the heat sink 50 adjacent to the sonde. Again, the heat sink shown in FIG. 5 is mounted at the same relative elevation on the sonde. The heat sink 50 also includes suitable fins. The fins are incorporated to ensure that the heat sink maintains the same temperature as the surrounding fluid media whether it is liquid or gaseous. The heat sink shown in FIG. 5 supports the resistor 44 which is constructed similar to the resistor 42 and which is mounted in a similar fashion. The heat sink 50 is larger to enable a resistor 54 to be mounted on the heat sink. The resistor 54 is connected to a suitable current source 60. The current source provides a fixed current flow for the resistor. The resistor 54 functions as a heat generator. Heat is transferred from the heated resistor to the heat sink 50. This heat is dissipated by the heat sink into the fluid.

A fixed rate of heat is generated by the resistor 54. The heat is formed at a fixed rate for the purpose of establishing a heat bias which is conducted away from the heat sink 50 by well fluid. This heating bias changes the temperature of the resistor 44 in contrast with the resistor 42 shown in FIG. 3. Perhaps this explanation can be assisted by a description of a typical set of circumstances.

Assume that the maximum temperature encountered in the bore hole is 400° F., and further assume that the resistor 54 is operated at 500° F. There is a rate of transfer of heat from the resistor 54 to the heat sink 50, the heat being dissipated into the surrounding well fluid. This rate of transfer is in part dependant on the temperature of the well fluid. Assume also that the variable resistors 42 and 44 (also shown mechanically mounted in FIGS. 3 and 5) are located at the same elevation on the sonde. When the sonde is lowered into a particular well fluid of unknown composition, both resistors 42 and 44 are heated to an ambient temperature. Assume for ease of discussion that they are heated from a surface temperature of 72° F. to 200° F. Since a common ambient temperatures is observed at both resistors 42 and 44, there is no output voltage formed at the bridge shown in FIG. 2 because the bridge legs are maintained at relative equal resistances because of ambient well temperature. However, the resistor 44 is operated at a higher temperature because the temperature of the heat sink 50 shown in FIG. 5 is elevated. Temperature increase arises from applying current to the resistor 54, thereby elevating the temperature at the resistor 54 to 500° F. in this example.

There is heat transfer from the resistor 54 to the heat sink. The rate of heat dissipation at the heat sink 50 depends substantially on the thermal conductivity of the surrounding fluid. Several representative thermal conductivity cooefficients were mentioned above. The heat transfer may well be a function of a single fluid (pure water as an example) or may be the heat transfer accomplished by a mixture such as oil and water. Thus, equation 1 is a suitable equation for mixed fluid heat transfer. Equation 1 is: $K_{effective} = K_1 F_1 + K_2 F_2$, Where
$K_1$ = temperature coefficient of Component 1
$K_2$ = temperature coefficient of Component
$F_1$ = Fraction of Component 1
$F_2$ = Fraction of Component 2.

In Equation 1, the various temperature cooefficients are identified as K while the various components which make up the mixture are identified by the factors F which is shown in Equation 1. For purposes of simplification, assume that only two components are present (oil and water as an example); such a mixture has a effective thermal conductivity coefficient given by Equation 2. Equation 2 is:

$$K_{effective} = K_1 F_1 + K_2(1 - F_1).$$

Assume that the sonde has been lowered to the point where it is exposed to a standing column of mixed oil and water where the ratio is 70% water and 30% oil. Assume further that the mixture sufficiently surrounds the heat sinks shown in FIGS. 3 and 5 to assure stabilization of the measurements. In that event, Equation 3 is derived from Equation 2 and thereby identifies the oil-water ratio: Rearranging, Equation 3 is:

$$F_1 = \frac{(K_{effective} - K_2)}{(K_1 - K_2)}$$

As will be seen, Equation 3 is obtained by simple rearrangement of the terms making up Equation 2 above. This yields a relatively simple relationship which can be measured quite easily and, hence, the oil and water ratio in the well fluid can be determined. The interface between the standing column of liquid or gas above the column of liquid can also be measured and determined.

From the foregoing, it will be understood how the thermal conductivity and, hence, the makeup of the fluids in the well bore can be determined. For instance, the fluids in the well bore are typically limited in composition. If liquid, they are typically water or oil or some mixture thereof. Even if it is ladened with drilling mud or is highly mineralized as in the instance of producing salt water, the thermal conductivity is still substantially determined by the oil and water which make up the liquids. Accordingly, a binary liquid system of oil and water (with or without other suspended ingredients) substantially comports with the relationship described above. The same is also true of frothy mixtures. In some wells, natural gas and liquid may mingle and form a froth in the bore hole. Again, the thermal conductivity of the froth will be determined as a binary system typically involving the gas which makes up the froth and the liquid. Thermal conductivity of methane and air can also be determined. Transitions or interfaces between gas and liquid can also be denoted.

As will be understood, the differential voltage signal output by the apparatus is therefore indicative of the thermal conductivity of the fluid adjacent to the sonde 10 and hence, the nature of the fluid can be determined, as for example, distinguishing oil from water, or mixtures thereof. While the foregoing is directed to the preferred embodiment, the scope thereof is determined by the claims.

What is claimed is:

1. For use with a sonde supported on a logging cable and adapted to be lowered into a well borehole, well fluid determining apparatus which comprises measuring means adapted to be supported on a sonde and lowered into the well bore hole for determining the thermal conductivity of fluid in the well bore hole and on the exterior of the sonde, said means including measuring circuit means connected to an exposed resistor, a heat sink having fins and joined to a mounting means, said mounting means being affixed to the sonde, said resistor protectively mounted between said fins, wherein said resistor is cooled by heat transfer provided by the well fluid, and said resistor is mounted on said mounting means exposing said resistor to the fluid in the well bore hole and on the exterior of the sonde, said measuring means forming an output signal indicative of the thermal conductivity coefficient of the fluid.

2. The apparatus of claim 1 further including means for providing temperature stability even when the ambient temperature of the well fluid varies in the well bore hole.

3. The apparatus of claim 1 including a heater means for forming heat which is transferred to temperature sensor means, said temperature sensor means forming an indication of temperature wherein the temperature is varied as a function of heat transfer away from the near vicinity by the fluid in the well bore hole.

4. The apparatus of claim 1 including a four legged resistance bridge circuit having a pair of output terminals across said bridge, and wherein two of the legs of said bridge are provided with externally mounted resistor means located on the exterior of apparatus enabling said resistor means to be exposed to well fluids within the well bore hole.

5. The apparatus of claim 1 further including a bridge circuit having four legs thereto, and wherein two of said legs are provided with impedance components which are exposed to the temperatures in the well bore hole to assure that said two legs track together and thereby cancel temperature variations arising from changes in ambient temperature.

6. The apparatus of claim 1 further including a bridge circuit having four legs thereto, and wherein two of said legs are provided with impedance components which are exposed to the temperatures in the well bore hole to assure that said two legs track impedances together and thereby cancel changes.

* * * * *